United States Patent
Barolak (10) Patent No.: US 9,690,000 B2
(45) Date of Patent: Jun. 27, 2017

(54) SYSTEM FOR MEASURING SHEAR STRESS IN DOWNHOLE TUBULARS

(71) Applicant: Baker Hughes Incorporated, Houston, TX (US)

(72) Inventor: Joseph Gregory Barolak, Spring, TX (US)

(73) Assignee: BAKER HUGHES INCORPORATED, Houston, TX (US)

(*) Notice: Subject to any disclaimer, the term of this patent is extended or adjusted under 35 U.S.C. 154(b) by 773 days.

(21) Appl. No.: 14/014,106

(22) Filed: Aug. 29, 2013

(65) Prior Publication Data

US 2014/0160889 A1 Jun. 12, 2014

Related U.S. Application Data

(60) Division of application No. 12/169,424, filed on Jul. 8, 2008, now Pat. No. 8,553,494, which is a continuation-in-part of application No. 11/622,101, filed on Jan. 11, 2007, now Pat. No. 7,660,197.

(51) Int. Cl.

| | | |
|---|---|---|
| *G01V 1/50* | (2006.01) | |
| *G01V 1/30* | (2006.01) | |
| *E21B 47/00* | (2012.01) | |
| *G01N 29/07* | (2006.01) | |
| *G01N 29/22* | (2006.01) | |
| *G01N 29/24* | (2006.01) | |
| *G01V 1/40* | (2006.01) | |

(52) U.S. Cl.
CPC ............ *G01V 1/30* (2013.01); *E21B 47/0006* (2013.01); *G01N 29/07* (2013.01); *G01N 29/225* (2013.01); *G01N 29/2412* (2013.01); *G01N 2291/02827* (2013.01); *G01N 2291/2636* (2013.01); *G01V 1/40* (2013.01); *G01V 1/50* (2013.01)

(58) Field of Classification Search
CPC ........ G01V 1/50; G01V 1/44; E21B 47/0005; E21B 47/0006
USPC ............................................ 367/35; 181/105
See application file for complete search history.

(56) References Cited

U.S. PATENT DOCUMENTS

| | | |
|---|---|---|
| 4,402,068 A | 8/1983 | Angehrn |
| 4,593,568 A | 6/1986 | Telford et al. |
| 4,708,204 A | 11/1987 | Stroud |
| 4,827,457 A | 5/1989 | Seeman et al. |
| 4,953,137 A | 8/1990 | Medlin |
| 5,197,038 A | 3/1993 | Chang et al. |
| 5,503,020 A | 4/1996 | Mandracchia |

(Continued)

FOREIGN PATENT DOCUMENTS

| | | |
|---|---|---|
| EP | 1467060 A1 | 10/2004 |
| EP | 1647669 A1 | 4/2006 |
| WO | 2004106913 A1 | 12/2004 |

OTHER PUBLICATIONS

Innerspec Technologies, EMAT Technology, http://www.innerspec.com/site/emat.asp, Oct. 10, 2006, pp. 1-2.

(Continued)

*Primary Examiner* — Ian J Lobo
(74) *Attorney, Agent, or Firm* — Mossman, Kumar & Tyler PC (57) ABSTRACT

An apparatus for evaluating the possibility of casing failure in a borehole measures azimuthal changes in a property responsive to azimuthal changes in axial stress. The measurements may be of acoustic velocity, magnetic permeability, and Barkhausen noise.

17 Claims, 9 Drawing Sheets

(56) References Cited

U.S. PATENT DOCUMENTS

| | | | |
|---|---|---|---|
| 6,098,021 | A | 8/2000 | Tang et al. |
| 6,268,911 | B1 * | 7/2001 | Tubel ............... E21B 23/03 |
| | | | 250/256 |
| 7,150,317 | B2 | 12/2006 | Barolak et al. |
| 7,234,519 | B2 | 6/2007 | Fripp et al. |
| 7,660,197 | B2 | 2/2010 | Barolak |
| 7,697,375 | B2 | 4/2010 | Reiderman et al. |
| 7,698,937 | B2 | 4/2010 | Neidhardt |
| 8,553,494 | B2 | 10/2013 | Barolak |
| 2005/0205268 | A1 | 9/2005 | Engels et al. |
| 2005/0224229 | A1 | 10/2005 | Blacklaw |
| 2006/0202700 | A1 | 9/2006 | Barolak et al. |
| 2007/0211572 | A1 | 9/2007 | Reiderman et al. |

OTHER PUBLICATIONS

NDT Resource Center, Pulser-Receivers, http://www.ndt-ed.org/EducationResources/ommunityCollegelUltrasonics/.. Oct. 5, 2006, pp. 1-2.
NDT Resource Center, Ultrasonic Measurement of Stress, http://www.ndt-ed.orgiEducationResources/CommunityCol-legelUltrasonics/ . . . Oct. 5, 2006, pp. 1-2.
NDT Resource Center, Electromagnetic Acoustic Transducers (EMATs), http://www.ndt -ed.org/EducationResources/Com-munityCollegelUltrasonics/ . . . Oct. 5, 2006, pp. 1-2.
NDT Resource Center, Precision Velocity Measurements, http://www.ndt-ed.org/EducationResources/CommunityCol-legelUltrasonics/ . . . Oct. 5, 2006, pp. 1-2.
Cantrell, Jr. et al.; "Relative Slope Invariance of Velocity-Stress and Strain-Stress Curves, Ultrasonics Symposium," 1981, pp. 434-437.
Frankel et al.; "Residual Stress Measurement in Circular Steel Cylinders," Ultrasonics Symposium, 1983, pp. 1009-1012.

* cited by examiner

SYSTEM FOR MEASURING SHEAR STRESS IN DOWNHOLE TUBULARS

CROSS-REFERENCES TO RELATED APPLICATIONS

This application is a divisional of U.S. patent application Ser. No. 12/169,424 filed Jul. 8, 2008, which is a continuation-in-part of U.S. patent application Ser. No. 11/622,101 filed on Jan. 11, 2007, now U.S. Pat. No. 7,660,197 issued Feb. 9, 2010, all of which are incorporated herein by reference in their entirety.

BACKGROUND OF THE DISCLOSURE

The present disclosure provides an apparatus and method for testing the structural integrity of tubing and casings used in a borehole. In particular, the present disclosure discusses an apparatus and method using ultrasonic waves to estimate the stress on tubulars in a borehole environment. The environmental conditions encountered by production casing and tubing used in hydrocarbon recovery can result in stress buildup in the tubing. This stress in the tubing may come from pressure and temperature variations during production, movement of the formation due to pressure depletion, "flow" of salt formations, etc. This stress may eventually lead to casing or tubing collapse or shear, rendering the well inoperable. Prior art methods have generally involved waiting for the buildup of this stress to a point where mechanical deformation occurs before the stress can be detected.

Stress buildup may also occur in a drillstring during the drilling of a borehole. During drilling operations, it is not uncommon for the drillstring to get stuck. To recover the stuck pipe, it is first required to determine the upper most 'free' point of the drillpipe. This is done by measuring the torque and/or pull induced from the surface or the physical stretching of the drillpipe due to this torque or pull.

Stress in a casing or tubing may be in the form of an axial load, circumferential torque, or a bending moment. Although stresses are applied on the drilling equipment while in use in the borehole environment, testing for wear typically occurs uphole or in a laboratory, often by observing the residual stress on the mandrel from its use. In general, when a stress is applied to a material and then removed, a residual stress remains on the material. This residual stress is often observed by checking for atomic dislocations at the crystalline level of the material and can be used to determine properties related to the structural integrity of the material. Various methods have been designed to observe residual stress on materials, including X-ray diffraction techniques, determining magnetic permeability, and ultrasonic testing.

Changes in ultrasonic wave propagation speed, along with energy losses from interactions with materials microstructures are often used to nondestructively gain information about properties of the material. An ultrasonic wave may be created in a material sample, such as a solid beam, by creating an impulse at one region of the sample. As the wave propagates through the sample, stresses and other material changes or defects affect the wave. Once the affected wave is recorded, the nature of the stresses of the material can be determined. Measurements of sound velocity and ultrasonic wave attenuation can be related to the elastic properties that can be used to characterize the texture of polycrystalline metals.

Velocity measurements are of interest in longitudinal waves propagating in gases, liquids, and solids. In solids, transverse (shear) waves are also of interest. The velocity of a longitudinal wave is independent of a sample's geometry when the dimensions at right angles to the sample are large compared to the sample area and to the wavelength. The velocity of a transverse wave is affected little by the physical dimensions of the sample. The relationship between stress and velocity has been discussed for example by Cantrell and Chern, "Relative Slope Invariance of Velocity-Stress and Strain-Stress Curves," Ultrasonics Symposium, 1981.

Measurement of ultrasonic velocity is performed by measuring the time it takes for a pulse of ultrasound to travel from one transducer to another (pitch-catch scenario) or return to the same transducer (pulse-echo scenario). Another measurement method compares the phase of the detected sound wave with that of a reference signal, wherein slight changes in the transducer separation are seen as slight phase changes, from which the sound velocity can be calculated. These methods are suitable for estimating acoustic velocity to about 1 part in 100. Standard practice for measuring velocity in materials is detailed in American Society for Testing and Materials (ASTM) Publication E494. Residual stress measurements in cylinders have been discussed for example by Frankel et al., "Residual Stress Measurement in Circular Steel Cylinders," Ultrasonics Symposium, 1983.

In petroleum exploration, time spent raising and lowering a drilling apparatus from and into a borehole is time that could otherwise be used in exploration and is thus costly. Historically, stress on a tubular containing drilling equipment used in a borehole has only been determined by looking for actual physical movement of the tubular (i.e., freepoint indicators) or by physical distortion of the tubular (i.e., casing inspection). Thus, it is desirable to perform stress testing of a drilling apparatus obtaining measurements downhole.

SUMMARY OF THE DISCLOSURE

One embodiment of the disclosure is an apparatus for identifying a shear stress in a tubular within a borehole. The apparatus includes a logging tool including at least one transducer configured to generate a wave in the tubular. The apparatus also includes a plurality of receivers azimuthally distributed in the logging tool. Each of the receivers is configured to produce a signal responsive to the generated wave and an azimuthal stress distribution in the tubular. The apparatus also includes at least one processor configured to determine from the signal from each of the plurality of receivers an indication of the azimuthal stress distribution in the tubular, and estimate from the indication of the azimuthal stress distribution a value of the bending stress in the tubular.

Another embodiment of the disclosure is a method of identifying a shear stress in a tubular within a borehole. The method includes using at least one transducer on a logging tool for generating a wave in the tubular, and using each of a plurality of receivers azimuthally distributed on the logging tool for producing a signal responsive to the generated wave and an azimuthal stress distribution in the tubular. The method further includes determining from the signal from each of the plurality of receivers an indication of the azimuthal stress distribution in the tubular, and estimating from the indication of the azimuthal stress distribution a value of the bending stress in the tubular.

Another embodiment of the disclosure is a computer-readable medium for use with an apparatus for identifying a shear stress a tubular within a borehole. The apparatus includes at least one transducer on a logging tool configured to generate a wave in the tubular, and a plurality of receivers azimuthally distributed on the logging tool, each of the plurality of receivers configured to produce a signal responsive to the generated wave and an azimuthal stress distribution in the tubular. The medium includes instructions that enable at least one processor to determine from the signal from each of the plurality of receivers an indication of the azimuthal stress distribution in the tubular, and estimate from the indication of the azimuthal stress distribution a value of the bending stress in the tubular. The medium may include a ROM, an EPROM, and EEPROM, a flash memory and/or an optical disk.

BRIEF DESCRIPTION OF THE DRAWINGS

For a detailed understanding of the present disclosure, reference should be made to the following detailed description of the disclosure, taken in conjunction with the accompanying drawing and in which.

DETAILED DESCRIPTION OF THE DISCLOSURE

The present disclosure is discussed with reference to specific logging instruments that may form part of a string of several logging instruments for conducting wireline logging operations. It is to be understood that the choice of the specific instruments discussed herein is not to be construed as a limitation and that the method of the present disclosure may also be used with other logging instruments as well.

Figure 1:
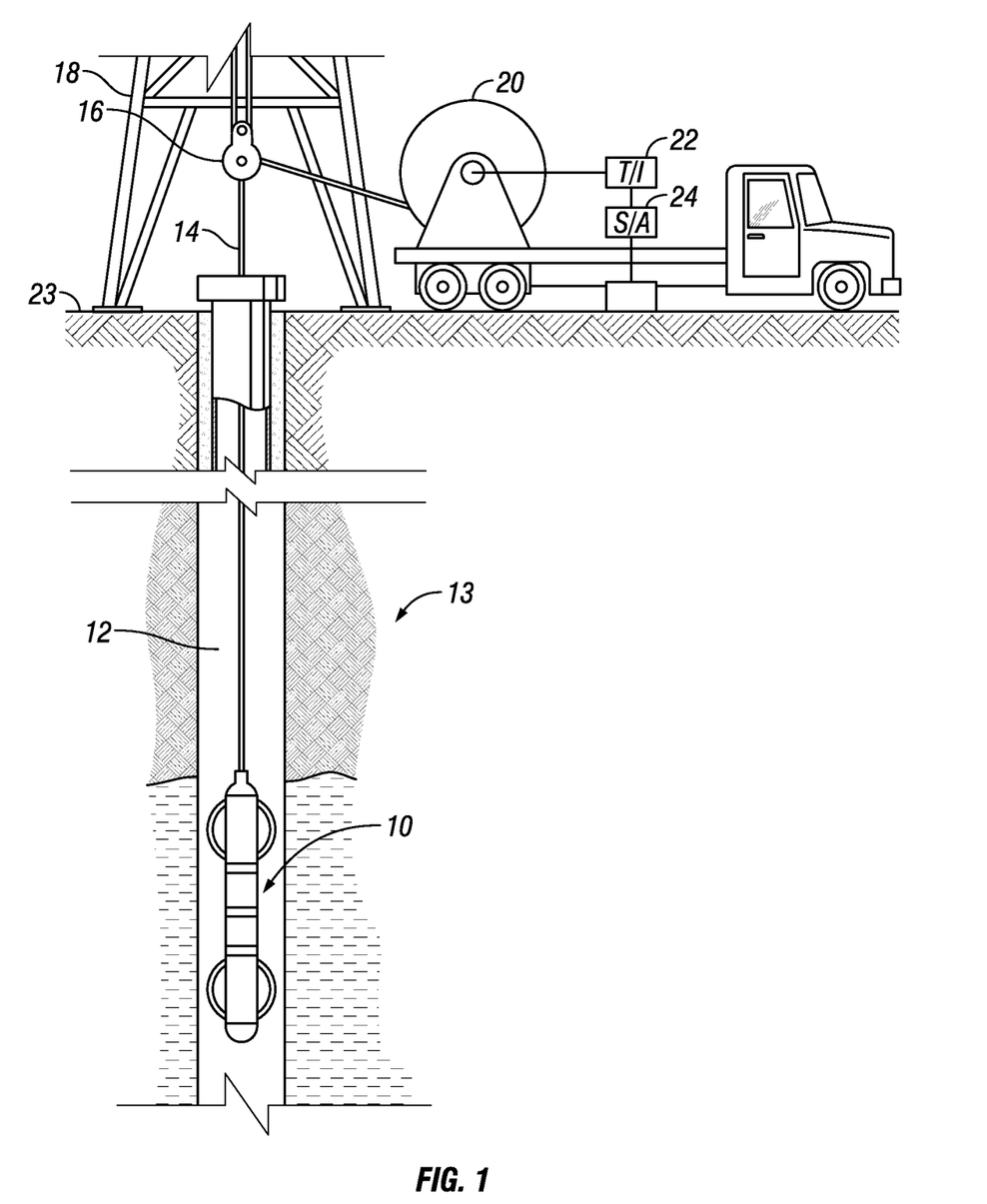
FIG. 1 is a schematic illustration of a wireline logging system.

FIG. 1 shows a logging tool 10 suspended in a borehole 12 that penetrates earth formations such as 13, from a suitable cable 14 that passes over a sheave 16 mounted on drilling rig 18. By industry standard, the cable 14 includes a stress member and seven conductors for transmitting commands to the tool and for receiving data back from the tool as well as power for the tool. The tool 10 is raised and lowered by draw works 20. Electronic module 22, on the surface 23, transmits the required operating commands downhole and in return, receives data back which may be recorded on an archival storage medium of any desired type for concurrent or later processing. The data may be transmitted in analog or digital form. Data processors such as a suitable computer 24, may be provided for performing data analysis in the field in real time or the recorded data may be sent to a processing center or both for post processing of the data. The system includes novel features that are discussed below.

Figure 2A:
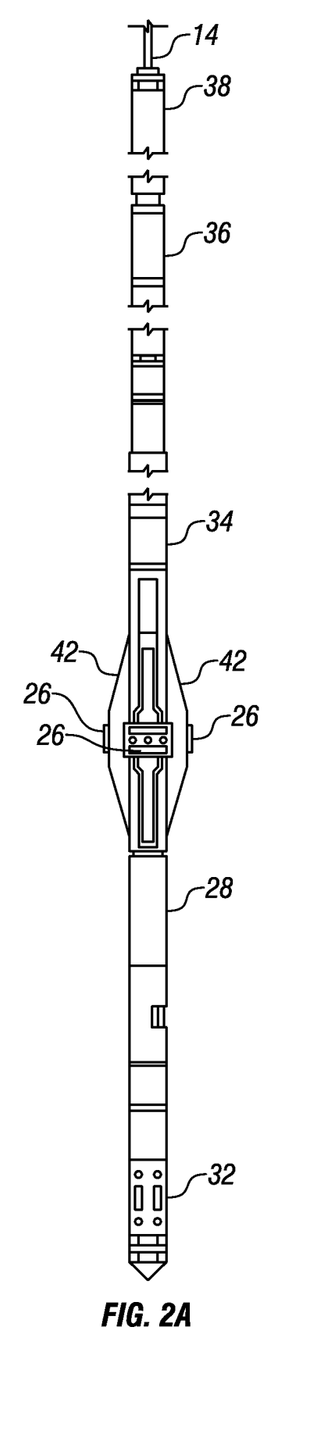
FIG. 2A is an illustration of a logging tool according to the present disclosure within a cased borehole with poor cementing.

FIG. 2A is a schematic external view of a borehole system according to the present disclosure. The tool 10 comprises the arrays 26 and is suspended from cable 14. Electronics modules 28 and 38 may be located at suitable locations in the system and not necessarily in the locations indicated. The components may be mounted on a mandrel 34 in a conventional well-known manner. In an exemplary assembly, the outer diameter of the assembly is about 5 inches and about fifteen feet long. An orientation module 36 including a magnetometer and an accelerometer or inertial guidance system may be mounted above the imaging assemblies 26 and 32. The upper portion 38 of the tool 10 contains a telemetry module for sampling, digitizing and transmission of the data samples from the various components uphole to surface electronics 22 (FIG. 1) in a conventional manner. If acoustic data are acquired, they are preferably digitized, although in an alternate arrangement, the data may be retained in analog form for transmission to the surface where it is later digitized by surface electronics 22.

Figure 2B:
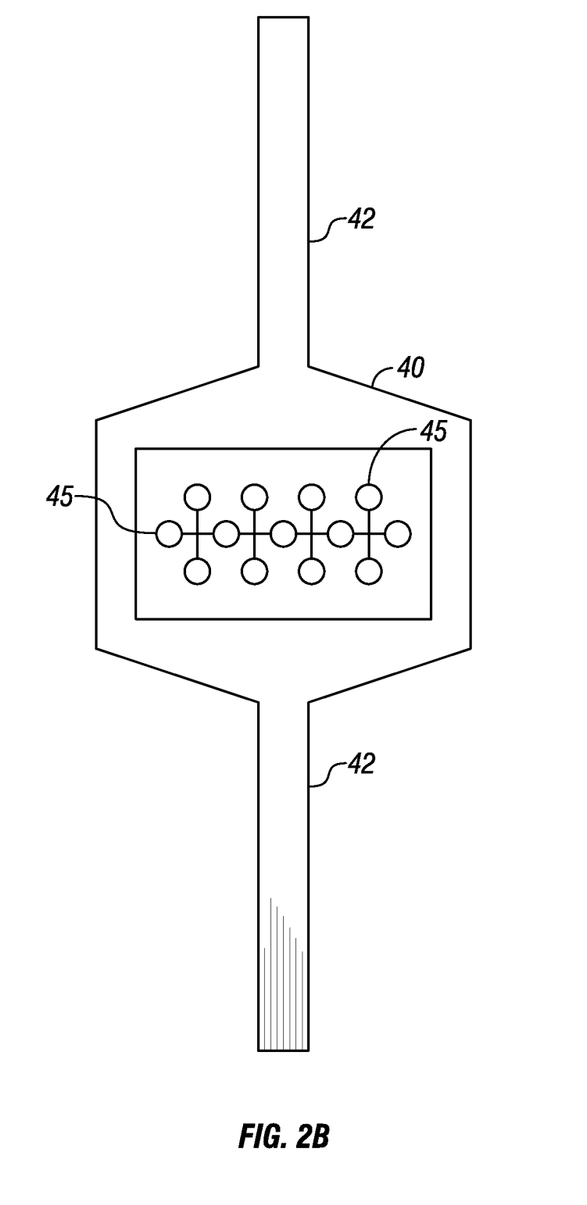
FIG. 2B shows an exemplary pad containing an array of transducers capable of performing the method of the present disclosure.

FIG. 2B shows an exemplary pad containing transducers capable of performing the method of the present disclosure. Pad 40 includes one or more acoustic sensors 45. In one embodiment of the disclosure, the acoustic sensors comprise electromagnetic acoustic transducers (EMATS) assembled in a pattern to obtain measurements of ultrasonic velocities for the purpose of determining a stress on a material. The pad 40 is attached to the mandrel 34 of FIG. 2A by way of supports 42. The pattern of EMATS shown in FIG. 2B is only an example of many possible configurations that may be used.

In another embodiment of the disclosure, the sensors may be disposed on two or more vertically spaced apart pads. Such an arrangement makes it easier to make axial measurements as a described below.

The present disclosure generally uses orthogonal acoustic velocity measurements in the steel tubulars to determine in-situ stress. In one possible embodiment, the velocity of a vibrational (acoustic) wave traveling axially in a casing is compared to the velocity of a similar wave traveling circumferentially at substantially the same point in the casing. Differences in the resulting measured velocities indicate either torque or axial stress in the casing. With a more complex arrangement using segmented circumferential or axial measurements, differences in axial stress around the circumference of the casing may indicate bending or crushing loads being applied to the casing by the formation. Also, localized stress measurements made in the area of casing corrosion or mechanical defects can be used to predict potential points of casing rupture. Since the properties of casing steel may vary, the use of orthogonal measurements is critical to identifying changes caused by stress from background changes in materials.

Measurement of acoustic travel time may be substituted with alternative measurements that are affected by casing stress. One alternative measurement might be magnetic permeability. The angle between the two measurements may be something other than orthogonal. A 90° angle, however, maximizes sensitivity of the measurement.

Measurements of stress in casing or tubing downhole have multiple potential uses. These uses potentially include casing deformation, freepoint indicators, and formation stresses (as transferred to the casing). The disclosed method offers a potential method of making an absolute stress measurement in a casing or tubing.

The present disclosure discusses an apparatus and method for performing acoustic testing on a casing or tubular. An ultrasonic wave can be produced at one location on the tubular and the wave can later be detected at the same or another location on the tubular. One way to create ultrasound within a material is via an EMAT. An EMAT comprises a magnetic element, such as a permanent magnet, and a set of wires. In general, the EMAT is placed against the material to be tested such that the set of wires are located between the magnetic element and the material to be tested. When a wire or coil is placed near to the surface of an electrically conducting object and is driven by a current at a desired ultrasonic frequency, eddy currents are induced in a near surface region. If a static magnetic field is also present, these currents experience a Lorentz force of the form $$\vec{F} = \vec{J} \times \vec{B} \qquad (1)$$

where $\vec{F}$ is a body force per unit volume, $\vec{J}$ is the induced dynamic current density, and $\vec{B}$ is the static magnetic induction. Thus the Lorentz force converts the electrical energy into a mechanical vibration, which can be used to test the material. Alternatively, EMATs may also be based on the use of magnetostrictive properties of the casing/tubing.

Since no coupling device is used between the EMAT and the tested material, the EMAT can operate without contact at elevated temperatures and in remote locations. Thus EMATs can eliminate errors associated with coupling variation in contact measurements and thereby provide precise velocity or attenuation measurements.

The coil and magnet structure used in an EMAT can be designed to excite complex wave patterns and polarizations. FIGS. 3A-3F shows a number of practical EMAT configurations including a biasing magnet structure, a coil configuration, and resultant forces on the surface of the solid for producing acoustic pulses using EMATS. The configurations of FIGS. 3A, 3B, and 3C excite beams propagating normal to the surface of a half-space and produce, respectively, beams with radial, longitudinal, and transverse polarizations. The configurations of FIGS. 3D and 3E use spatially varying stresses to excite beams propagating at oblique angles or along the surface of a component. These configurations are considered for illustrative purposes although any number of variations on these configurations can be used.

Figure 3A:
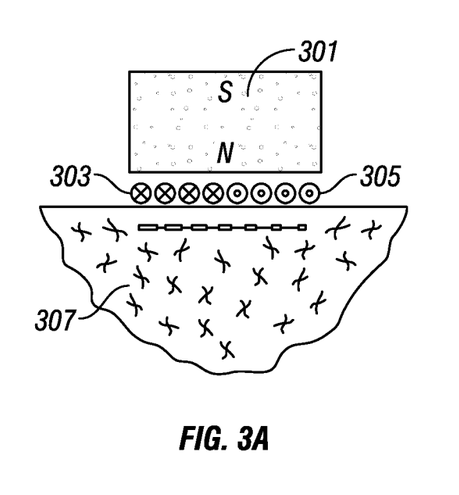
FIGS. 3A-E shows various practical transducer configurations that may be used on a material and resultant forces on the surface of the material for producing acoustic pulses.

FIG. 3A shows a cross-sectional view of a spiral coil EMAT configuration for exciting radially polarized shear waves propagating normal to the surface. Permanent magnet 301 and tubular 307 are separated by a space containing a wire represented by one or more wires as shown as wire segments 303 and 305. The wire segments 303 and 305 represent separate groups of wire segments carrying current in anti-parallel directions in the manner illustrated in FIG. 3A, thereby exciting the radially polarized shear waves propagating normal to the surface.

Figure 3B:
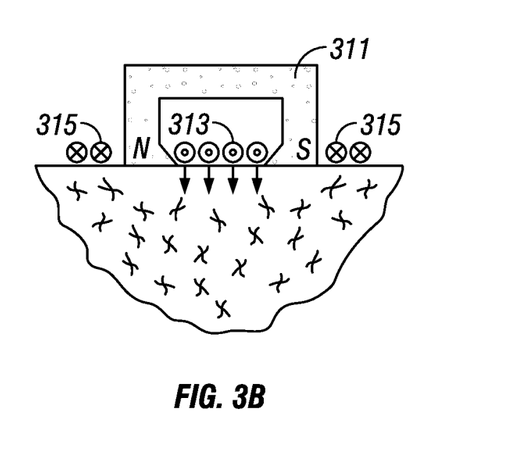

FIG. 3B shows a cross-sectional view of a tangential field EMAT configuration for exciting longitudinally polarized compressional waves propagating normal to the surface. Permanent magnet 311 is placed against tubular to produce a magnetic field parallel to the surface. A magnet such as the magnet 311 of FIG. 3B having a horseshoe configuration may be used. Wires segments 313 provide a current flowing between the magnetic poles perpendicular to the direction of the local magnetic field of magnet 311. Wire segments 315 provide a current flowing anti-parallel to the current in wire segments 313 in a region exterior to the magnetic poles.

Figure 3C:
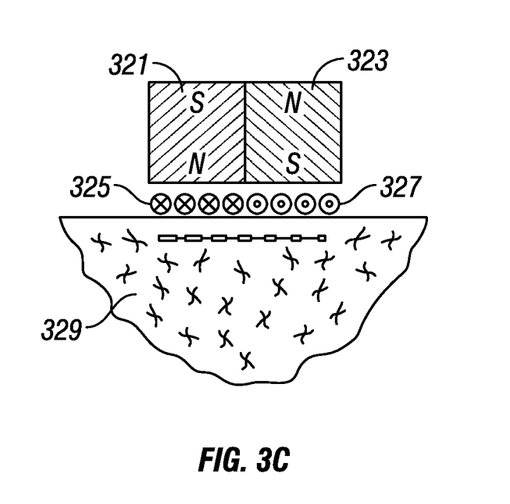

FIG. 3C shows a cross-sectional view of a normal field EMAT configuration for exciting plane polarized shear waves propagating normal to the surface. The configuration comprises a pair of magnets 321 and 323 assembled so as to provide two anti-parallel magnetic fields at the surface of the tubular. The permanent magnets 321 and 323 are separated from tubular 329 by a space containing one or more wires 325 and 327 providing anti-parallel current.

Figure 3D:
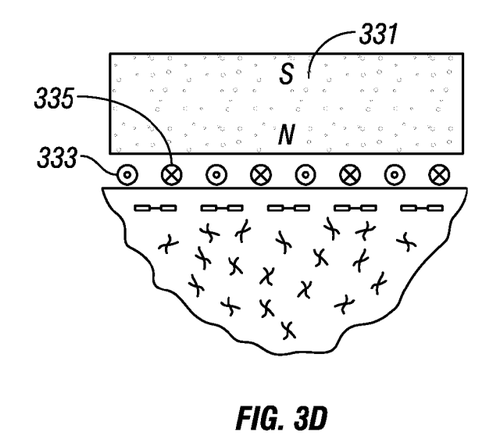

FIG. 3D shows a cross-sectional view of a meander coil EMAT configuration for exciting obliquely propagating L (long) or SV waves, Rayleigh waves, or guided modes (such as Lamb waves) of plates. The configuration includes a permanent magnet and tubular separated by a space containing wire segments such as one or more wires 333 and 335 which provides current flowing in sequentially alternating directions.

Figure 3E:
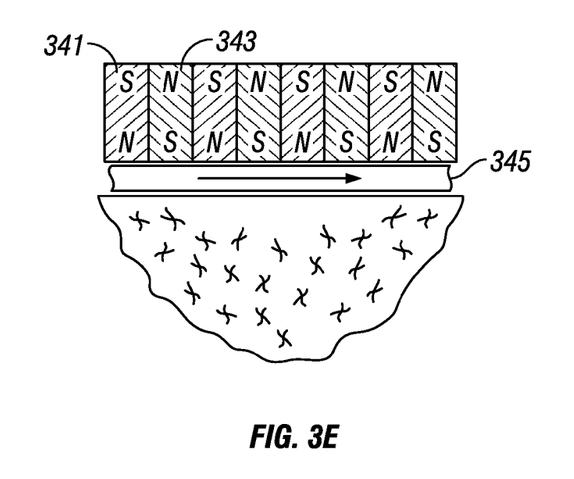

FIG. 3E shows a cross-sectional view of a periodic permanent magnet EMAT for exciting grazing or obliquely propagating horizontally polarized (SH) waves or guided SH modes of plates. Multiple permanent magnets such as magnets 341 and 343 are assembled so as to provide alternating magnetic polarities at the surface of the tubular. The magnetic assembly and tubular are separated by a space containing a wire 345 that provides a current in a single direction.

For sheet and plate specimens experiencing applied or residual stress, the principal stresses $\sigma_a$ and $\sigma_b$ may be inferred from orthogonal velocity measurements. Eq. (2) relates ultrasonic velocities to the principle stresses experienced in a sheet or plate:

$$2\rho V_{avg}[V(\theta) - V(\theta + \pi/2)] = \sigma_a - \sigma_b \qquad (2).$$

In Eq. (2), $V_{avg}$ is the average shear velocity and $\rho$ is a density of a material. $V(\theta)$ and $V(\theta + \pi/2)$ are mutually perpendicular wave velocities as can be detected at a transducer. It is understood that velocity difference $V(\theta) - V(\theta + \pi/2)$ is maximized when the ultrasonic propagation directions are aligned with the principal stress axes. The magnitude of this difference, along with the density and mean velocity can be used to estimate the principal stress difference.

Figure 4:
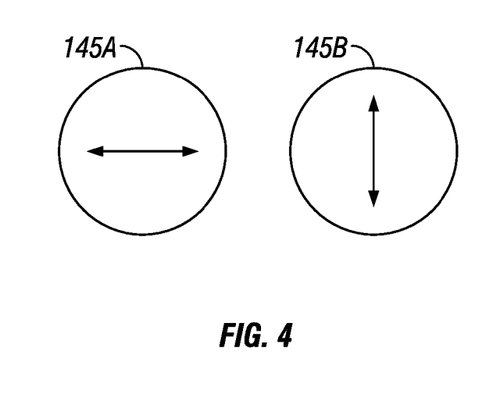
FIG. 4 is a schematic illustrations of two EMATs configured to generate shear-waves in two different directions.

FIG. 4 shows an arrangement of two EMATS 145A and 145B. The pad 40 illustrated and FIG. 2B is not shown. When EMATS 145A and 145B are of the type shown in FIG. 3E, they will produce horizontally polarized shear-wave propagating along the tool axis and circumferential to the tool axis, thus providing the necessary measurements for solving eqn. (2). Those versed in the art would appreciate that using an array of transducers as shown in FIG. 2B, it would be possible to generate horizontally polarized shear waves propagating in different directions. The EMATs, in addition to acting as transmitters, can also act as receivers, so that by having two EMATs with the same polarization at different spatial positions, it is possible to determine the velocity of propagation of the wave. In addition, by having such transducers mounted on different pads on the downhole logging to it is possible to make measurements of the stress differences circumferentially around the borehole.

By using transducers of the type shown in FIG. 3B it would be possible to make measurements of compression velocity at different azimuthal positions along the borehole. Variations in this velocity are indicative of circumferential variations of the stress. The same is true using transducers of the type shown in FIG. 3C. But using transducers of the type shown in FIG. 3D it would be possible to generate Rayleigh waves on land waves along the surface of the tubular.

In addition, those versed in the art would recognize that the velocity of propagation of a vertically polarized shear-wave may differ from the velocity of propagation of the horizontally polarized shear-wave in the same direction. This difference may also be indicative of the stress in the tubular. Such measurements may be obtained by using transducers of the type shown in FIGS. 3D and 3E.

In one embodiment a velocity of an acoustic wave traveling axially in the casing is compared to the velocity of a similar wave traveling circumferentially at substantially the same point in the casing. Differences in the measured velocities are indicative of torque or axial stress in the casing. With a more complex arrangement using segmented circumferential or axial measurements made with pad-mounted EMATs, differences in axial stress around the circumference of the casing are indicative of bending a crushing load being applied to the casing by the formation. Localized test measurements made in the area of casing corrosion or mechanical defects are used to predict potential points of casing failure. As would be known to those versed in the art, such casing corrosion or mechanical defects would produce changes in the stress field. All of these use measurements having orthogonal direction of propagation or orthogonal polarization or both. Properties of casings steel may vary, so that the use of such measurements is important in identifying changes caused by stress from changes caused by differences in the steel.

Figure 5:
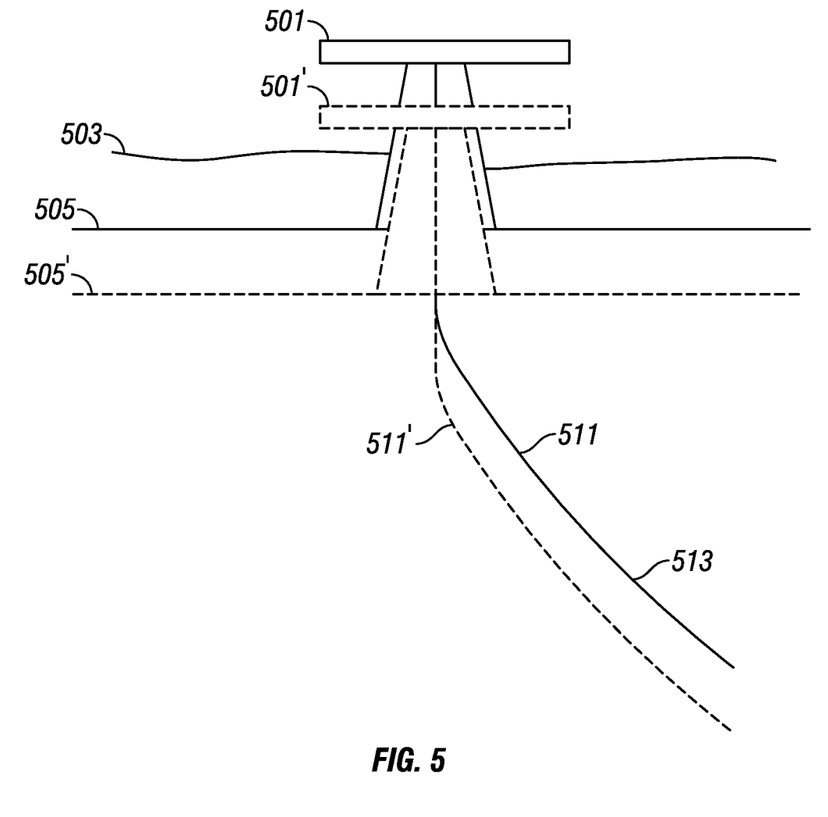
FIG. 5 illustrates bending of casing resulting from subsidence of the ocean bottom upon which a platform is located.

Turning now to FIG. 5, an important application of the methods of stress determination discussed above is illustrated. Shown is a production platform 501 resting on an initial position of the ocean bottom 505. The surface of the ocean is depicted by 503. Over time, production of hydrocarbons from the subsurface commonly leads to subsidence of the ocean bottom. The new positions of the ocean bottom and the production platform are denoted by 505' and 501' respectively. As an example, subsidence of the ocean bottom at the Ekofisk field in the Norwegian portion of the North Sea was 5.5 m after 25 years of production and continuing at the rate of 0.5 m/year. As a result of this subsidence, an extensive portion of the production casing 511 may be deformed, the deformed position being denoted by 511'. The portion of the casing that is relatively undisturbed is denoted by 513.

Those versed in the art would recognize that such large displacements of the casing introduce large stresses and can lead to significant weakening and potential catastrophic failure of the casing. For this reason, it is important to be able to identify the stresses before they get to the point where the casing is near its yield point.

Figure 6A:
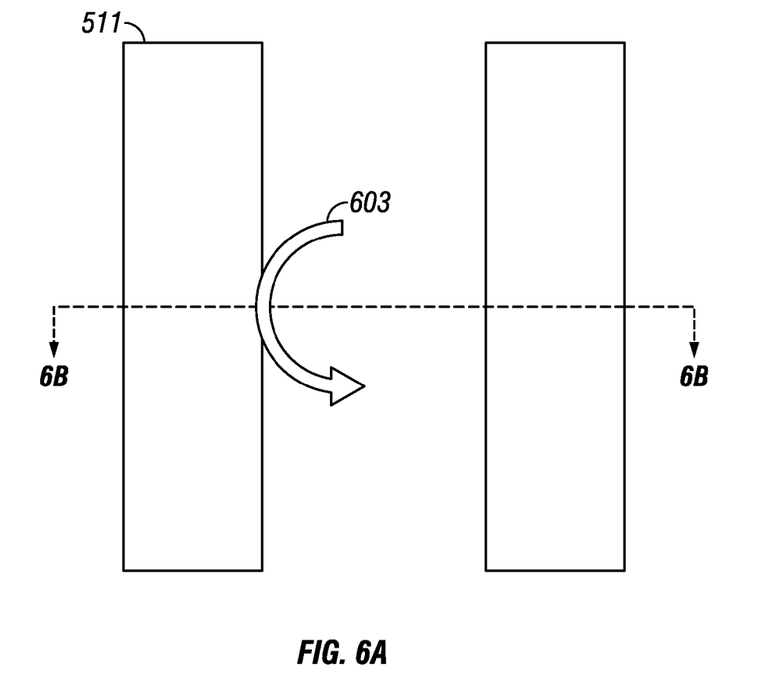
FIGS. 6A, 6B shows the differential axial stresses resulting from torsion on a casing.

One embodiment of the disclosure envisages using acoustic velocity measurements of the type discussed above to identify the stresses in the casing. FIG. 6A shows an exemplary casing 511. The effect of the subsidence is to subject the casing to a bending or shear stress such as 603. Such a bending stress is easily seen to occur if the casing is initially not vertical, but may also occur when the casing is initially vertical. In the latter case, buckling of the casing is the dominant mode of deformation, but the local bending or shear stress is still the determining factor for casing failure.

Figure 6B:
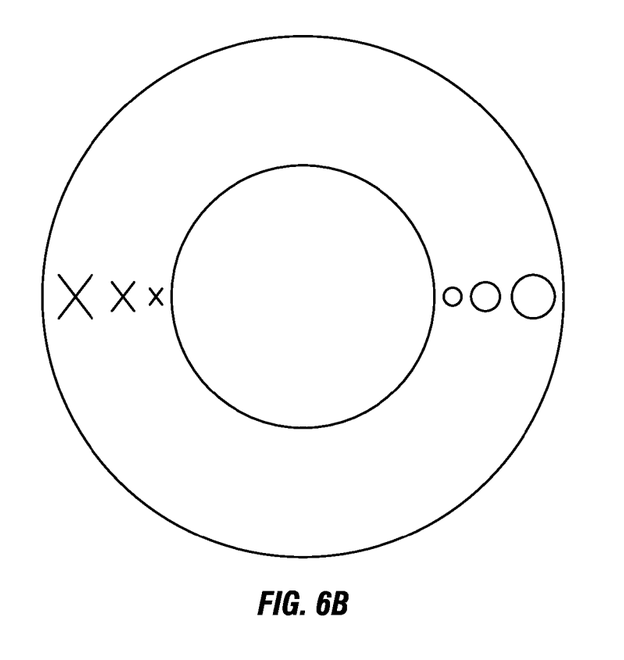

Shown schematically in FIG. 6B are the axial stresses resulting from the bending stress 603. In the right half of the casing, the stress may be extensional while the left half of the casing, the stress may be compressional. The stresses increase with radial distance from the center of the casing, depicted by the size of the x's and o's. In an azimuth that is 90° to that shown, the axial stresses will be zero. It should be noted that the terms "compressional" and "extensional" are to be construed in a relative sense: what is important is the difference in axial stress between the sides of the casing that are azimuthally 180° apart. Thus, using the transducer arrangements described above, it is possible to estimate changes in the axial stress as a function of azimuth and radial distance from the center of the borehole. These can be used in conjunction with known methods to predict the possibility of failure prior to the deformation of the casing approaching the failure point.

Another embodiment of the disclosure measures changes in magnetic permeability as a stress indicator. A suitable tool for the purpose is disclosed in FIGS. 7A, 7B. The tool is provided with an axially oriented exciter coil 740 on a suitable location of the mandrel 34 and the pad(s) are provided with one or more transversely oriented receiver coils 701a, . . . 701n. With a plurality of such pads, it is possible to get a full 360° azimuthal coverage of the casing in the borehole. The exciter coil 740 is driven at a preselected low frequency and the voltage induced in the receiver coils 701a, . . . 701n is related to the magnetic permeability of the casing near the receiver coil. Receiver coil voltage logs are run to give an indication of the changes in the magnetic permeability of the casing with azimuthal direction. The principle behind this has been discussed in U.S. Pat. No. 4,708,204 to Stroud and requires the measurement of the induced current in an axially oriented receiver coil in both an unstressed and a stressed condition.

As noted in Stroud magnetic flux induced into the drill pipe by an input signal will produce eddy currents which will in turn create an electromagnetic field. This secondary magnetic field produced by eddy current flow in the casing may be detected by a receiving coil. If the input signal as well as all other variables are held constant then the signal on the receiving coil will vary in amplitude and phase as a function of the magnetic permeability of the pipe. As discussed in Stroud, stress changes in the casing result in changes in magnetic permeability which, in turn, affects the induced current in an axially oriented coil. In the present disclosure, the transversely oriented coils provide an indication of azimuthal stress changes in magnetic permeability. An azimuthal plot of the magnetic permeability can thus pinpoint directions of maximum and minimum principal stress, and the magnitude of the difference between the maximum and minimum permeability is an indication of the difference between the maximum and minimum axial stress. This method does not require measurements made in an unstressed condition. The method can thus be used to identify imminent casing failure as discussed with reference to FIGS. 5-6B. It is anticipated that the embodiments shown in FIGS. 7A, 7B would have an operating frequency in the range of 100-500 Hz, though this is not to be construed as a limitation. Similarly, the embodiment disclosed in FIG. 7C, discussed next, is expected to operate in a frequency range of 500 Hz to 5 KHz.

Figure 7A:
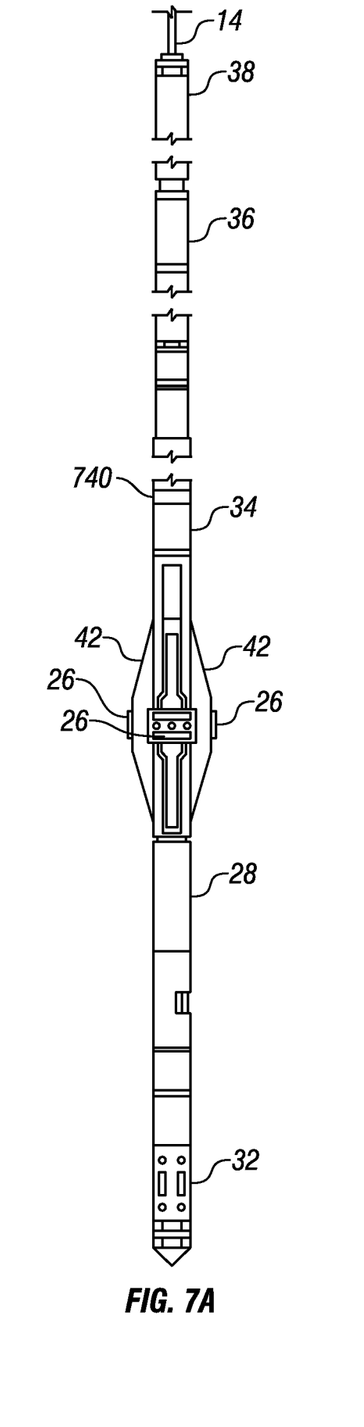
FIGS. 7A, 7B and 7C show an embodiment of the disclosure in which magnetic permeability changes may measured.
Figure 7B:
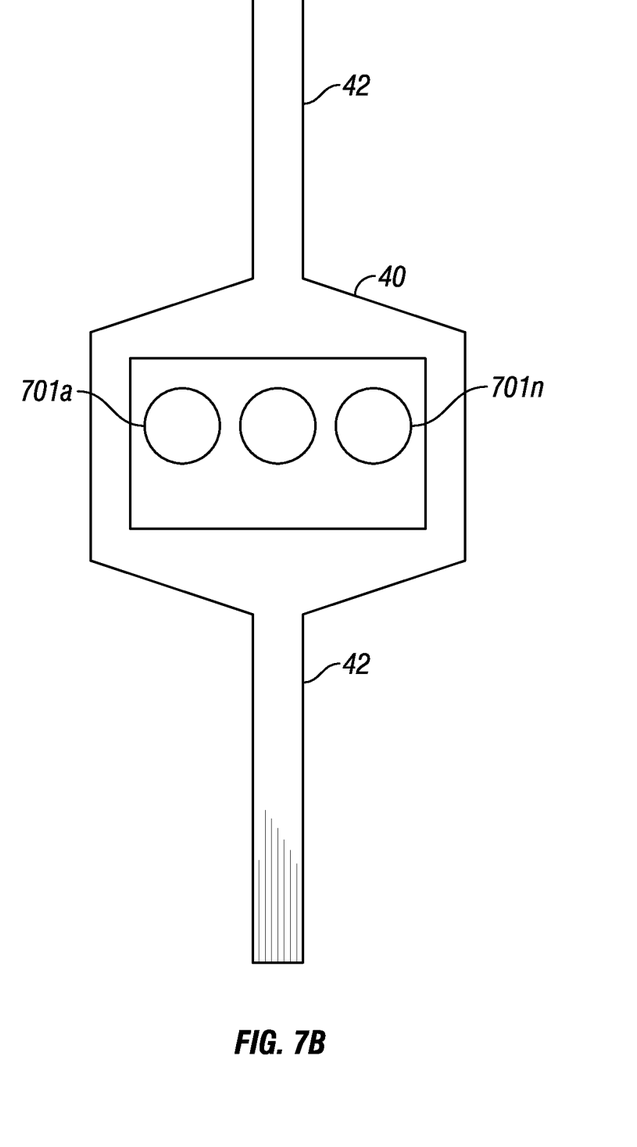
Figure 7C:
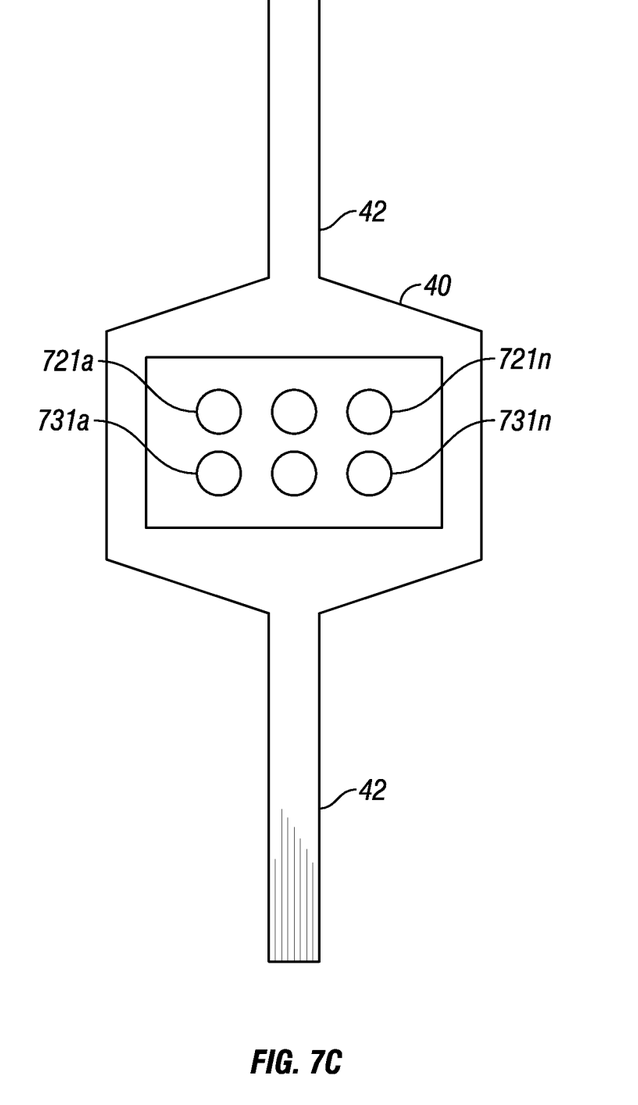

Turning next to FIG. 7C, an arrangement in which both the exciter coil and the receiver coil are transversely oriented is shown. In principle, the received signal with both the exciter and the receiver being transversely oriented will have a higher signal level than one in which only the receivers are transversely oriented (as in FIG. 7B). In addition, the distance between the exciter coils 721a . . . 721n and the receiver coils 731a . . . 731n is less than the distance between the exciter coil 740 and the receiver coils 701a . . . 701n. This too will give an improved signal level. A potential drawback is the need to have the exciter coils 721a . . . 721n in FIG. 7C properly calibrated.

Figure 8A:
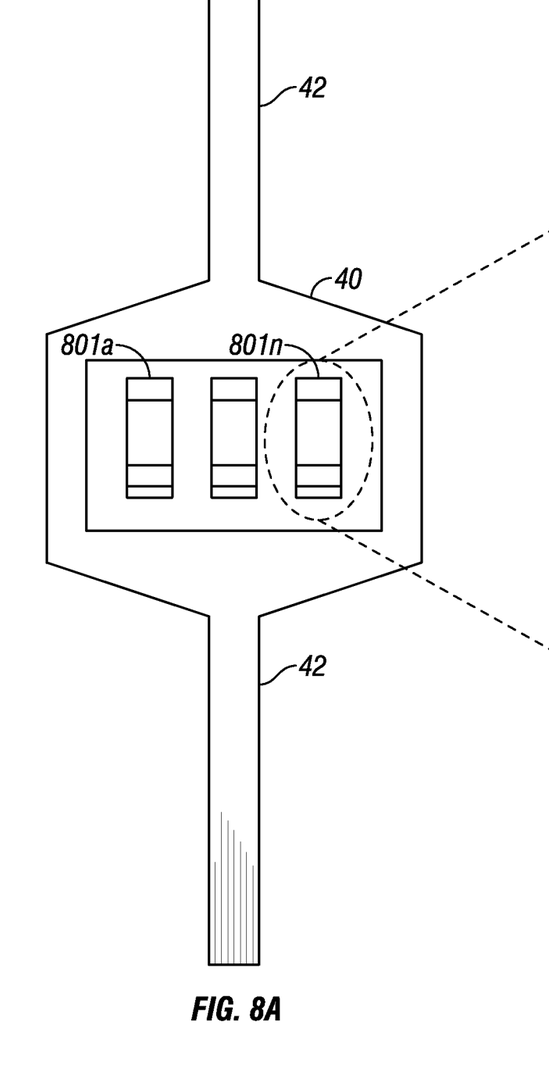
FIG. 8A-B shows an embodiment of the disclosure in which noise resulting from the Barkhausen effect is used.
Figure 8B:
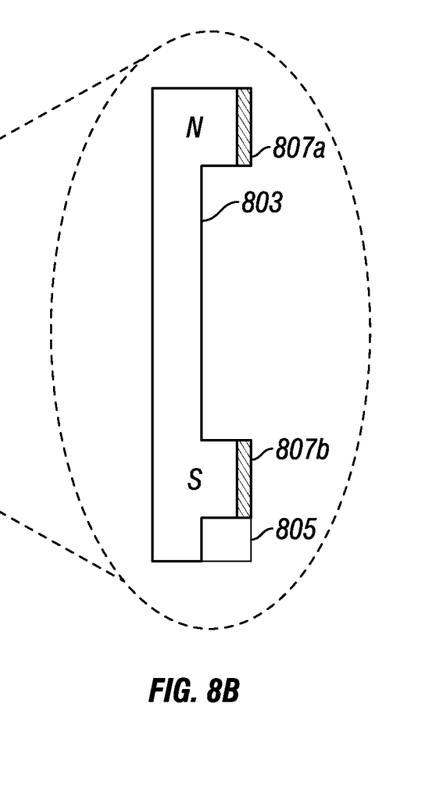

Turning now to FIGS. 8A-8B, another embodiment of the disclosure is shown. In this case, the sensor pad 40 is provided with a plurality of sensors 801a, . . . 801n. An axial cross-section of a sensor is shown in FIG. 8B. The sensor comprises a magnet 803, the poles of which are in contact with the formation by ferromagnetic brushes. As the tool is axially pulled up the borehole, the magnetic flux density in the casing wall immediately below the brush 807b is less than in the region of the casing between the brushes 808a, 807b. There is a significant change in the magnetic flux density directly below the brush 807b. As the tool is moved, this results in a changing direction of magnetic field that produces a reorientation of magnetic domains in the casing. This results in Barkhausen noise. The Barkhausen noise is detected by an inductive or other type of magnetic field sensor 805 positioned in a vicinity of the brush 807b in the casing. The Barkhausen noise level is measured as a function of azimuth, and the azimuthal variation is related to azimuthal change in the magnetic permeability and azimuthal change in the axial stress in the casing. For the purposes of the present disclosure, the moving permanent magnet arrangement 803, 807a, 807b may be regarded as a transmitter that reorients magnetic domains in the casing and the magnetic field sensor 805 is a receiver responsive to changes in the magnetic field.

For each of the embodiments disclosed in FIGS. 6-8, knowing the elastic properties of the casing and the variation in acoustic or magnetic properties with stress, it is possible to use a table lookup to estimate the bending stress to which the casing is being subjected, and thus take appropriate remedial action to avoid casing failure.

The first embodiment of the disclosure has been described above is a specific example of using EMATS as the acoustic sensors. This is not to be construed as a limitation on the disclosure. The method of the disclosure could also be carried out using other side types of sensors such as piezoelectric transducers and wedge transducers. Wedge transducers are discussed, for example, in U.S. Pat. No. 4,593,568 to Telford et al.

The disclosure has been described above with reference to a device conveyed on a wireline. However the method of disclosure may also be practices using the tool conveyed on a tubular such as a drillstring or coiled tubing, or on a slickline.

Implicit in the processing method of the present disclosure is the use of a computer program implemented on a suitable machine readable medium that enables the processor to perform the control and processing. The machine readable medium may include ROMs, EPROMs, EAROMs, Flash Memories and Optical disks. Such a computer program may output the results of the processing, such as the stress constraints, to a suitable tangible medium. This may include a display device and/or a memory device.

What is claimed is:

1. A method of determining an azimuthal stress variation in a tubular within a borehole, the method comprising:
using at least one transducer on a logging tool for generating a wave in the tubular;
using each of a plurality of receivers azimuthally distributed on the logging tool for producing a signal responsive to the generated wave and an azimuthal stress variation in the tubular, comprising using, for each of the plurality of receivers, an electromagnetic receiver mounted on a pad extendable from a body of the logging tool and wherein the signal produced by each of the plurality of receivers is indicative of a magnetic permeability of the tubular; and
determining from the signal from each of the plurality of receivers an indication of the azimuthal stress variation in the tubular.

2. The method of claim 1 further comprising estimating from the indication of the azimuthal stress variation a value of a shear stress in the tubular.

3. The method of claim 1 further comprising using, for the at least one transmitter, a plurality of electromagnetic transmitters mounted on a pad extendable from a body of the logging tool.

4. The method of claim 1 further comprising:
using the at least one transmitter to reorient a magnetic domain in the tubular; and
using, for the at least one receiver, a magnetic flux sensor responsive to the reorientation of the magnetic domain.

5. The method of claim 1 further comprising using, for the at least one transmitter and the plurality of receivers at least one of: (i) an electro-magnetic acoustic transducers, (ii) a piezoelectric transducers, and (iii) a wedge transducer.

6. The method of claim 5 further comprising positioning the plurality of receivers on at least one pad extendable from a body of a logging tool.

7. The method of claim 1 further comprising using a lookup table for estimating the value of the shear stress from the indication of the azimuthal stress variation.

8. The method of claim 1 further comprising conveying the logging tool into the borehole on one of: (i) a wireline, (ii) a drilling tubular, (iii) a slickline, and (iv) coiled tubing.

9. The method of claim 1 further comprising selecting the tubular from the group consisting of: (i) production tubing, (ii) casing, and (iii) a drilling tubular.

10. The method of claim 1 comprising determining from the signal from each of the plurality of receivers an indication of the azimuthal stress variation in the tubular prior to failure of the tubular.

11. A method of determining an azimuthal stress variation in a tubular within a borehole, the method comprising:
determining from a signal responsive to a wave generated in a tubular by a transducer on a logging tool from each of a plurality of acoustic receivers azimuthally distributed on the logging tool an indication of the azimuthal stress variation in the tubular, comprising determining the azimuthal stress variation in the tubular using estimated orthogonal components of the wave.

12. The method of claim 11, wherein the tubular comprises casing, the method further comprising predicting from the indication of the azimuthal stress variation a point of casing rupture.

13. The method of clam 11 wherein each of the plurality of receivers comprises an electromagnetic receiver mounted on a pad extendable from a body of the logging tool and wherein the signal produced by each of the plurality of receivers is indicative of a magnetic permeability of the tubular.

14. The method of clam 11 further comprising generating the wave.

15. The method of claim 11 comprising determining from a signal responsive to a wave generated in a tubular by a transducer on a logging tool from each of a plurality of acoustic receivers azimuthally distributed on the logging tool an indication of the azimuthal stress variation in the tubular prior to failure of the tubular.

16. A method of determining an azimuthal stress variation in a tubular within a borehole, the method comprising:
using at least one transducer on a logging tool for generating a wave in the tubular by reorienting a magnetic domain in the tubular;
using each of a plurality of receivers azimuthally distributed on the logging tool for producing a signal responsive to the generated wave and an azimuthal stress variation in the tubular, comprising using, for each of the plurality of receivers, a magnetic flux sensor responsive to the reorientation of the magnetic domain; and determining from the signal from each of the plurality of receivers an indication of the azimuthal stress variation in the tubular.

17. A method of determining an azimuthal stress variation in a tubular within a borehole, the method comprising:

determining from a signal responsive to a wave generated in a tubular by a transducer on a logging tool from each of a plurality of acoustic receivers azimuthally distributed on the logging tool an indication of the azimuthal stress variation in the tubular, wherein each of the plurality of receivers comprises an electromagnetic receiver mounted on a pad extendable from a body of the logging tool and wherein the signal produced by each of the plurality of receivers is indicative of a magnetic permeability of the tubular.

* * * * *